United States Patent [19]
Liu et al.

[11] Patent Number: 6,093,200
[45] Date of Patent: *Jul. 25, 2000

[54] COMPOSITE BIOABSORBABLE MATERIALS AND SURGICAL ARTICLES MADE THEREFROM

[75] Inventors: Cheng-Kung Liu, Norwalk; Ying Jiang, North Haven; Mark S. Roby, Killingworth; Steven L. Bennett, Southington; Richard P. Stevenson, Colchester; Jeffrey P. Pietrangeli, Bridgeport, all of Conn.

[73] Assignee: United States Surgical, Norwalk, Conn.

[ * ] Notice: This patent issued on a continued prosecution application filed under 37 CFR 1.53(d), and is subject to the twenty year patent term provisions of 35 U.S.C. 154(a)(2).

[21] Appl. No.: 08/926,728

[22] Filed: Sep. 10, 1997

Related U.S. Application Data

[63] Continuation of application No. 08/371,623, Jan. 12, 1995, which is a continuation-in-part of application No. 08/194,766, Feb. 10, 1994, Pat. No. 5,626,611.

[51] Int. Cl.[7] .................................................. A61B 17/04
[52] U.S. Cl. ............................. 606/228; 606/231
[58] Field of Search .................. 606/228, 231, 606/151

[56] References Cited

U.S. PATENT DOCUMENTS

| | | | |
|---|---|---|---|
| 3,630,205 | 12/1971 | Listner | 606/228 |
| 3,987,797 | 10/1976 | Stephenson | 606/228 |
| 4,563,392 | 1/1986 | Harpell et al. | 428/394 |
| 5,102,420 | 4/1992 | Hunter et al. | 606/231 |
| 5,147,383 | 9/1992 | Bezwada et al. | 606/228 |
| 5,260,013 | 11/1993 | Samuelson | 264/105 |
| 5,269,807 | 12/1993 | Liu | 606/228 |
| 5,279,783 | 1/1994 | Liu et al. | 606/228 |
| 5,387,383 | 2/1995 | Collier et al. | 264/105 |
| 5,464,424 | 11/1995 | O'Donnell, Jr. | 606/228 |

FOREIGN PATENT DOCUMENTS 0523743   7/1992   European Pat. Off. .

*Primary Examiner*—Michael Buiz
*Assistant Examiner*—Tina T. D. Pham

[57] ABSTRACT

Composite materials have a core portion formed from a biocompatible material and at least one shell portion of a biocompatible material joined to the core portion. In a preferred embodiment, the core portion is coextruded with the shell portion to form a composite filament or sheet. The composite materials may be used as sutures or formed into medical devices or surgical articles for implantation within a living organism.

13 Claims, 4 Drawing Sheets

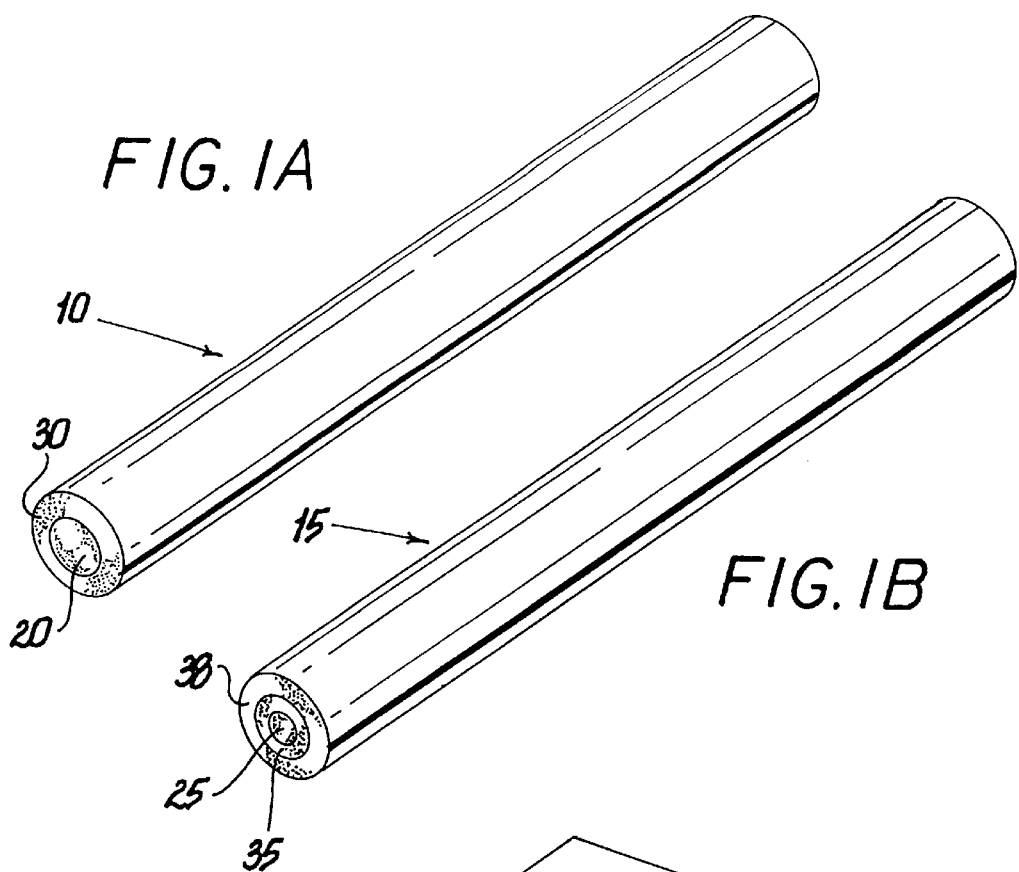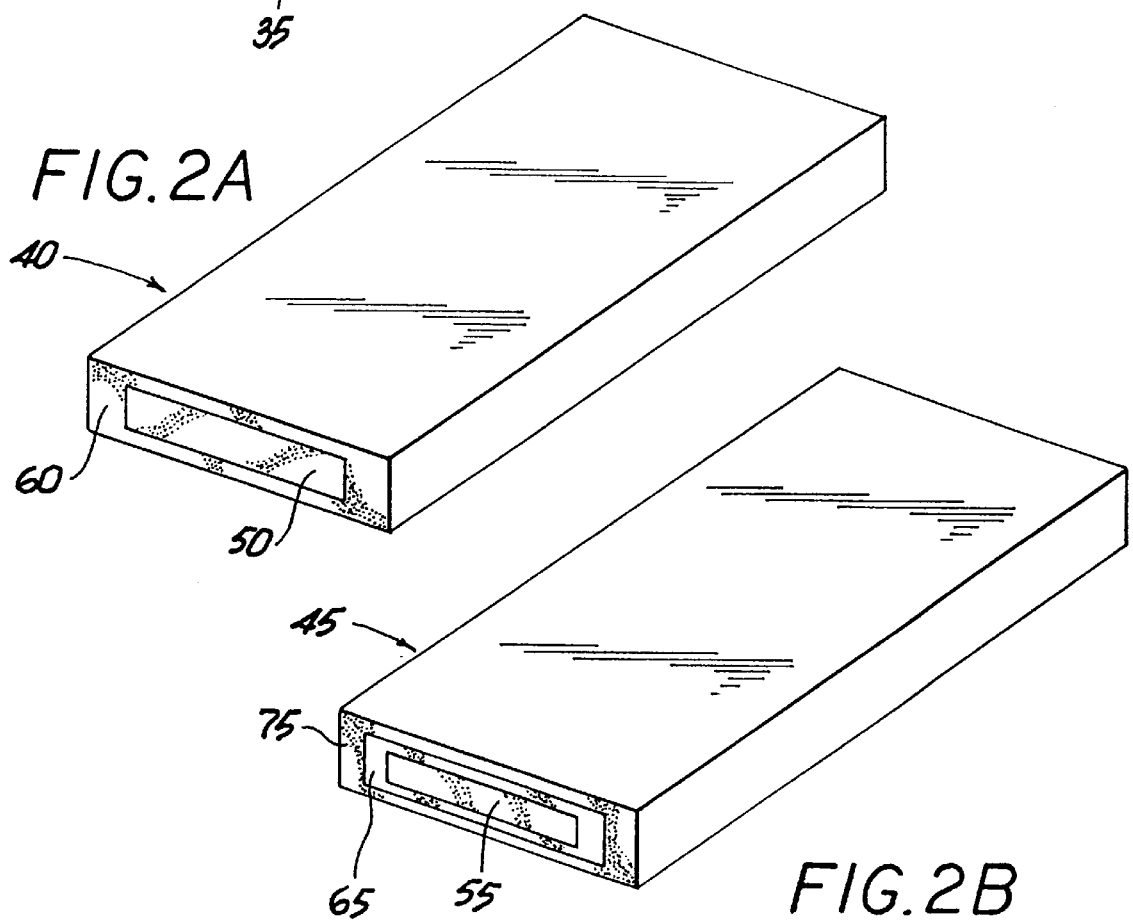

COMPOSITE BIOABSORBABLE MATERIALS AND SURGICAL ARTICLES MADE THEREFROM

RELATED APPLICATION

This is a continuation of copending application Ser. No. 08/371,623 filed on Jan. 12, 1995 which is a continuation-in-part of application Ser. No. 08/194,766 filed on Feb. 10, 1994, U.S. Pat. No. 5,626,611.

BACKGROUND

1. Technical Field

This disclosure relates to biocompatible materials and, more particularly, to biocompatible composite materials such as filaments and sheets. The composite includes a core of a first material and at least one shell joined to the core, the shell being formed of a second material.

2. Background of Related Art

Bioabsorbable materials are known in the art for a variety of uses, particularly those uses in which the bioabsorbable material is implanted within a living organism for medical purposes. The term "bioabsorbable" is used to describe a material capable of being broken down into smaller constituents which can be metabolized and/or excreted by a living organism. Hydrolysis is one mechanism by which many bioabsorbable materials are broken down following implantation within a living organism. Such materials are useful for temporarily holding tissues in a desired position during healing, and being absorbed by the organism after a period of time.

Various bioabsorbable materials and medical devices made therefrom are known in the art See, e.g., U.S. Pat. Nos. 2,668,162; 2,703,316; 2,758,987; 3,225,766; 3,297,033; 3,422,181; 3,531,561; 3,565,077; 3,565,869; 3,620,218; 3,626,948; 3,636,956; 3,736,646; 3,772,420; 3,773,919; 3,792,010; 3,797,499; 3,839,297; 3,867,190; 3,878,284; 3,982,543; 4,047,533; 4,052,988; 4,060,089; 4,137,921; 4,157,437; 4,234,775; 4,237,920; 4,300,565; 4,429,080; 4,441,496; 4,523,591; 4,546,152; 4,559,945; 4,643,191; 4,646,741; 4,653,497; and, 4,741,337; U.K. Patent No. 779,291; D. K. Gilding et al., "Biodegradable polymers for use in surgery—polyglycolide/poly(lactic acid) homo- and copolymers: 1", Polymer, Volume 20, pages 1459–1464 (1979), and D. F. Williams (ed.), *Biocompatibility of Clinical Implant Materials, Vol II*, ch. 9: "Biodegradable Polymers" (1981).

Fiber-reinforced compositions used for surgical implants have been described in U.S. Pat. Nos. 4,279,249; 4,550,449; 4,539,931; 4,743,257; 5,080,665. The fiber-reinforcements in these compositions provide increased strength and rigidity as may be required for bone repair, but render these compositions unsuitable where flexibility is required.

It would be desirable to provide an implantable composite having a bioabsorption rate which varies over time and which is suitable for use in making a variety of medical devices, including those in which flexibility is a desirable characteristic.

SUMMARY

Composite materials in accordance with this disclosure have a core portion formed from a first biocompatible material and at least one shell portion formed from a second biocompatible material joined to the core portion. The first and second biocompatible materials can be bioabsorbable materials having different rates of bioabsorption. In a particularly useful embodiment, the core portion is coextruded with the shell portion to form a composite filament or sheet. In another embodiment, a polypropylene monofilament is prepared having a syndiotactic polypropylene shell portion and an isotactic polypropylene core portion. The materials disclosed herein may be used as sutures or formed into medical devices or surgical articles for implantation within a living organism.

BRIEF DESCRIPTION OF THE DRAWINGS

FIG. 1A illustrates a filament having a core portion and a shell portion according to the present disclosure.

FIG. 1B illustrates a filament having a core portion and plural shell portions according to the present disclosure.

FIG. 2A illustrates a sheet having a core portion and a shell portion according to the present disclosure.

FIG. 2B illustrates a sheet having a core portion and plural shell portions according to the present disclosure.

DETAILED DESCRIPTION OF THE PREFERRED EMBODIMENTS

Figure 3:
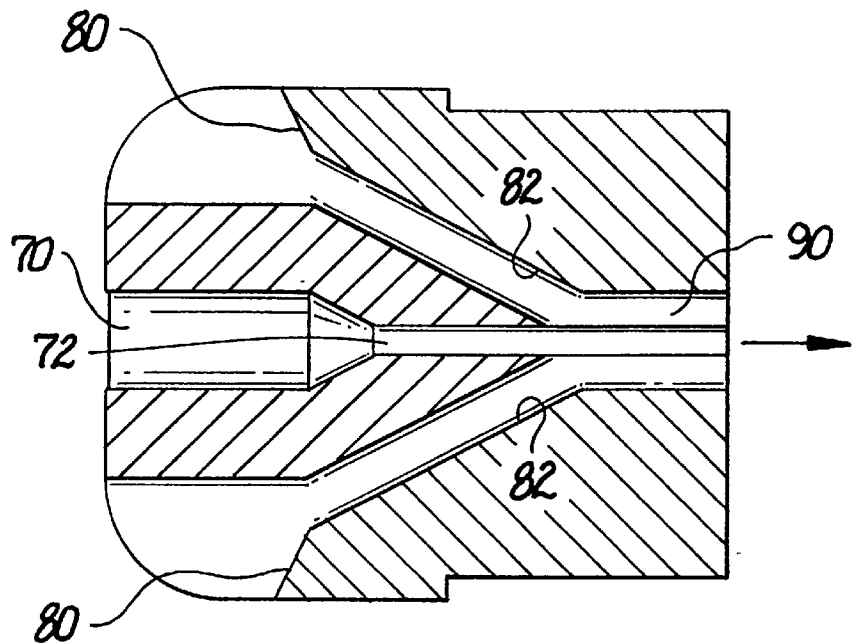
FIG. 3 is a coextrusion die optionally used to form a composite filament according to the present disclosure.

Referring now in detail to the drawings, FIG. 1A shows a filament 10 having a core portion 20 surrounded by a shell portion 30. Shell portion 30 is joined to core portion 20 in such a manner that the two portions form a single, structural element, i.e., filament 10. As such, filament 10 is a composite material in which all of the constituent elements contribute to the properties of the overall structure. Thus, filament 10 differs from coated filaments in that the coatings of such filaments, even for very thick coatings, do not contribute substantially to the strength of the filament.

FIG. 1B illustrates a composite filament 15 having a core portion 25, a first shell portion 35, and a second shell portion 38. In this embodiment, three separate materials may be used to form portions 25, 35, and 38 or the outer shell 38 may be the same material as the core portion 25. It is within the scope of this disclosure to produce filaments having any number of shell portions, depending upon the desired application of the filament.

FIG. 2A shows a composite sheet 40 having a core portion 50 and a shell portion 60. As with the composite filament of FIG. 1, the composite sheet 40 is fabricated so that the core 50 is joined to shell 60 such that the sheet behaves as a unified structural entity.

FIG. 2B shows a composite sheet 45 having a core portion 55 and shell portions 65 and 75. As with the composite filament of FIG. 1B, the sheet of FIG. 2B may include any number of shell portions, depending upon its ultimate use.

The dimensions of the core portion and shell portion can vary widely depending on a number of factors including the materials from which the composite is made and the intended use of the composite. Generally, the thickness of the core portion can range from about 0.001 mm to 10 mm or more, and the thickness of the shell portion can range from about 0.0001 mm to about 10 mm or more. For example, when the intended use is as a suture, a composite having a generally cylindrical core portion made from polydioxanone with a diameter in the range of about 0.01 mm to about 0.8 mm, with a shell portion made from polycaprolactone having a thickness of about 0.001 mm to about 0.5 mm will provide a filament having acceptable flexibility and strength. Where a more rigid, rod-like structure is desired, for example to be used as an osteosynthesis device, a generally cylindrical core portion made from polyglycoilde with a diameter in the range of about 0.1 mm to about 1.0 mm with a shell portion made from polydiaxanone and having a thickness of about 0.001 mm to about 0.2 mm will provide suitable rigidity and strength. For laminated sheet-like composites, useful for example as an adhesion barrier, hernia repair device, organ support, artificial skin substrate, bone plate, or stent, a core portion made from polyglycolide having a thickness of about 0.001 mm to about 5 mm having a shell portion made from polydioxanone and having a thickness of about 0.01 mm to about 0.25 mm joined to at least one side of the core portion would provide a composite with suitable physical characteristics.

In particularly useful embodiments, the core portion and shell portion are substantially co-extensive. It is also contemplated, however, that composites wherein the shell portion only partially covers the core portion can be made in accordance with this disclosure.

In a preferred embodiment, the materials used to form the core and shell portions of composite filament 10 and composite sheet 40 are bioabsorbable materials. Bioabsorbable materials used to form the core portions of these composites include, but are not limited to absorbable polymers made from glycolide, glycolic acid, lactide, lactic acid, caprolactone, dioxanone, trimethylene carbonate and dimethyl trimethylene carbonate. Copolymers (block or random) and mixtures and blends of such polymers or copolymers are also useful. Particularly useful absorbable polymers for the core portion include glycolide/lactide copolymers, polycaprolactone and polydioxanone.

Bioabsorbable materials used to form the shell portions of the composite filaments and sheets include, but are not limited to, absorbable polymers made from glycolide, glycolic acid, lactide, lactic acid, caprolactone, dioxanone, trimethylene carbonate and dimethyl trimethylene carbonate. Copolymers, (block or random) and mixtures and blends of such polymers and/or copolymers are also useful. Particularly useful polymers for the shell portion include polydioxanone, polycaprolactone, polylactide and polytrimethylene carbonate.

In one preferred embodiment, the material used to form the core portion of the composite material has a higher rate of bioabsorption than the material used to form the shell portion of the composite material. This embodiment provides a strong, fiber-forming core material combined with a flexible shell material to provide a strong and flexible composite. Such core materials include, but are not limited to, bioabsorbable polymers, copolymers, or mixtures fabricated from glycolide or glycolic acid. Particularly preferred glycolide-containing polymers include copolymers of glycolide and lactide having 90% glycolide and 10% lactide, copolymers of glycolide and lactide having 92.5% glycolide and 7.5% lactide, and copolymers of glycolide and lactide having 18% glycolide and 82% lactide.

Materials having a lower rate of hydrolysis relative to the above glycolide-containing polymers are used to form the shell portion of the above composite material. Such relatively lower hydrolysis rate materials include bioabsorbable polymers, copolymers, or mixtures fabricated from polydioxanone, polylactide, polycaprolactone, and polytiimethylene carbonate.

Particularly preferred combinations for composite materials having a core with a higher rate of hydrolysis than the shell include, but are not limited to: a core of a copolymer of 18% glycolide and 82% lactide with a shell of polydioxanone; a core of a copolymer of 92.5% glycolide and 7.5% lactide with a shell of polydioxanone; a core of a copolymer of 25% glycolide and 75% lactide backfllled with glycolide as shown in U.S. Pat. No. 4,844,854 with a shell of polydioxanone; a core of a triblock copolymer glycolide and dioxanone (as described above) with a shell of polycaprolactone; and a core of polydioxanone with a shell of polycaprolactone.

In another preferred embodiment, the material used to form the core portion of the composite material has a lower rate of bioabsoiption than the material used to form the shell portion of the composite material. A higher rate of bioabsorption for the shell may, in some applications, serve to enhance tissue ingrowth and subsequent healing and wound closure. In this embodiment, the core may be of bioabsorbable polymers, copolymers, or mixtures fabricated from polydioxanone, polycaprolactone, and polytrimethylene carbonate. The shell may be of bioabsorbable polymers, copolymers, or mixtures fabricated from glycolide or glycolic acid. Particularly preferred glycolide-containing polymers include copolymers of glycolide and lactide having 90% glycolide and 10% lactide, copolymers of glycolide and lactide having 92.5% glycolide and 7.5% lactide, and copolymers of glycolide and lactide having 18% glycolide and 82% lactide.

It is also contemplated that materials of the same composition can be used for both the core and the shell portions. However, the morphology of the material of the core layer is selected to be different from the morphology of the material of the shell layer such that the two layers have different rates of bioabsorption. In general, it is known that amorphous polymers have higher rates of hydrolysis than crystalline versions of the same polymer. For example, the core material may be formed from an amorphous glycolide-containing polymer while the shell may be formed from a crystalline glycolide-containing polymer. Materials may be added to the polymer melt during formation of the composite material to promote crystallinity in the shell layer.

Although the above descriptions of preferred embodiments focus on bioabsorbable polymers, it is understood that those of skill may select any two bioabsorbable materials having different rates of bioabsorption to construct a bioabsorbable composite having the desired strength and bioabsorption characteristics needed for a particular medical or surgical application. Such bioabsorbable materials include, but are not limited to, collagen, chitin, chitin derivatives (e.g., chitosan), amino acid polymers (e.g., gelatin), and polysaccharides (e.g., dextran).

In yet another embodiment, composite materials having a core/shell structure may be fabricated using non-absorbable, biocompatible materials. Such materials include biocompatible polymeric materials which may be used in applications requiring a more permanent implantation of a prosthetic device. Core and shell polymeric materials include polyesters (e.g., polyalkyl terephthalates), polyamides (e.g., nylon), polyurethanes, polycarbonates, polyamides, fluoropolymers, polyolefins, vinyl polymers, etc.

Particularly preferred combinations include coextruded polyester and polyurethane fibers, coextruded low order and high order nylons such as nylon 6 or nylon 66 with nylon 12, and coextruded syndiotactic polypropylene and isotactic polypropylene. Biocompatible implants such as sutures, soft tissue patches, surgical mesh, wound dressings, surgical felts, vascular grafts, nerve repair devices, artificial skin and sternum tape may be fabricated from the composite biocompatible materials.

The present composite filaments and sheets may be fabricated by a number of known polymer processing techniques. One preferred technique is coextrusion. Extrusion is a polymer processing technique in which a viscous melt is fed, under pressure, through a die in a continuous stream. In coextrusion, plural polymer melt streams feed through individual flow channels to be shaped as a single polymeric article. The polymer melts may be combined in several ways. Plural melts may be extruded separately from a single die, plural melts may be extruded partly separately followed by combined extrusion, or plural melts may be coextruded together.

Figure 4:
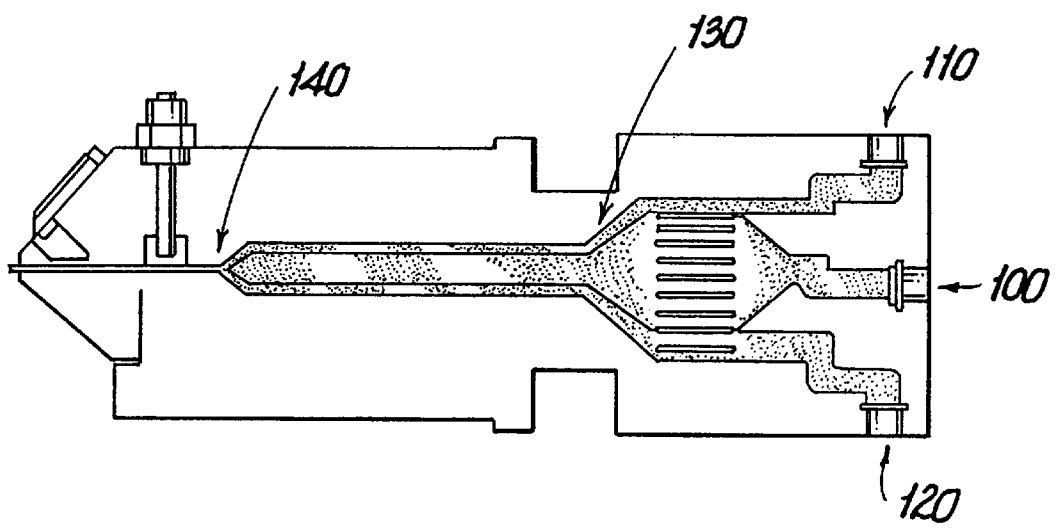
FIG. 4 is a coextrusion die optionally used to form a composite sheet according to the present disclosure.

A coextrusion die which may be used to form a composite filament according to the present disclosure is illustrated schematically in FIG. 3. In FIG. 3, the polymer melt used to form core 20 of filament 10 passes through central flow channel 70 where it is shaped as it passes through channel exit 72. The polymer melt used to form the shell 30 of filament 10 passes through outer flow channel 80 where it is shaped as it passes through channel exit 82. The two concentric polymer melts are joined at die exit 90, forming a continuous polymer melt A coextrusion die which may be used to form a composite sheet according to the present disclosure is schematically depicted in FIG. 4. In FIG. 4, the polymer used to form core portion 50 of sheet 40 is fed from an extruder to flow channel 100. The polymer used to form shell portion 60 of sheet 40 is fed from extruders to flow channels 110 and 120. The melts are in region 130 of the die and are formed into a sheet in region 140.

The dies and methods described above with reference to FIGS. 3 and 4 are exemplary of coextrusion techniques used to form filaments and sheets. Any coextrusion process may be used to form the bioabsorbable composite filaments and sheets. Examples of other coextrusion processes suitable for use in forming the present materials as well as examples of suitable extrusion apparatus which may be used with the dies of FIGS. 3 and 4 are found in Vols. 4 and 6 of the *Encyclopedia of Polymer Science and Engineering*, (John Wiley & Sons, New York), c. 1986, pp. 812–832 and 571–631, respectively, which are incorporated by reference herein.

Figure 5:
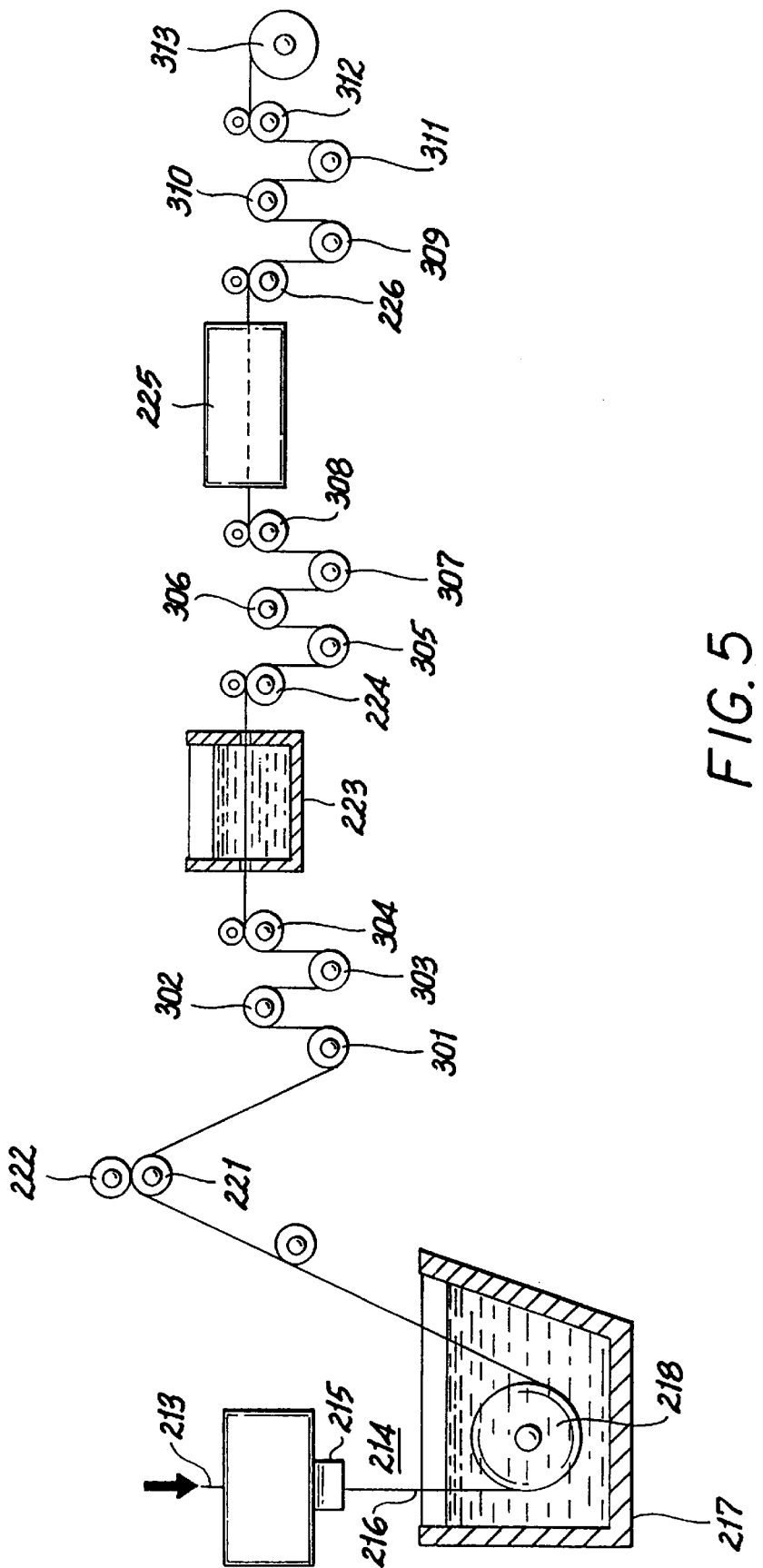
FIG. 5 schematically illustrates a spinning process used to form filaments according to the present disclosure.

In another preferred embodiment, the composite materials may be spun into fibers to be used as monofilament or multifilament sutures. An exemplary spinning process is schematically illustrated in FIG. 5. To produce fibers having the core/shell structure of FIG. 1, the core and shell constituent materials are separately melted. The constituent materials are separately fed as polymer melts 213 to spinneret 215 and are combined in the manner shown in FIG. 3 just before the spinneret exit orifice. Although a single filament is shown for clarity in FIG. 5, it is understood that spinnerets having any desired number of exit orifices in a range of exit diameters may be used.

Molten monofilament 216 exits spinneret 215, passes through air gap 214, and enters quench bath 217. Air gap 214 is the distance between the spinneret exit and bath 217. Preferably, the air gap distance ranges from 0.5 to 100 centimeters and, more preferably, from about 1 to 20 centimeters. As monofilament 216 passes through bath 217, it solidifies. In a preferred embodiment, quench bath 217 is a water bath.

Within the quench bath, filament 216 is driven by drive roller 218. As it emerges from the bath, a wiper may optionally remove excess water. Monofilament 216 wraps around a first godet 221 and is prevented from slipping by nip roll 222. Godets 301, 302, 303, and 304 engage and drive the filament prior to a stretching operation. The number of godets is not critical; any suitable godet system may be employed in the present spinning process.

During stretching, monofilament 216 is drawn through hot water bath 223 by godets 224, 305, 306, 307, and 308 or any other suitable arrangement. This second godet system rotates at a higher speed than that of godet 104 to provide a desired stretch ratio.

Following stretching, monofilament 216 may be annealed within hot air oven chamber 225, driven by godets 226, 309, 310, 311, or 312, or any other suitable drawing system. Take-up reel 313 winds the finished monofilament product.

Other suitable fiber manufacture processes, including other spinning processes, which may be used to form the present composite materials are described in Volume 6 of the *Encyclopedia of Polymer Science and Engineering*, (John Wiley & Sons, New York), c. 1986, pp. 802–839, the disclosure of which is incorporated by reference herein.

Other polymer processing techniques may be used to form the composite filaments and sheets. These include, but are not limited to, casting, injection molding, and blow molding. In short, any polymer processing technique capable of creating composite materials having shell portions adequately joined with core portions are contemplated to form the present composite bioabsorbable materials.

In general, the formation of a composite depends on both materials being heated to a temperature at which fusion of at least the surface of the materials begins. Where coextrusion is the method used to from the composite, both materials are heated to a temperature above their respective melting points. Where pressing is used to from the composites, the combination of temperature and pressure should be such that at least the surface of the core portion and the surface of the shell portion in contact therewith begin to fuse so that the two portions are joined into a unitary structure.

As will be appreciated by those skilled in the art, a certain amount of mixing of the core and shell materials will occur at the interface of those two portions. The amount of mixing may be only at the molecular level and thus, as a practical matter undetectable. However, in some instances the amount of mixing may be sufficient to produce a micro-shell layer at the interface between the shell and core portions. This micro-shell layer is made from a mixture of the core and shell materials and has its own bioabsorption profile.

The composite biocompatible materials disclosed herein may be used to form various surgical devices. The composite filaments may be used as monofilament sutures or combined to make multifilament sutures. The filaments may be woven to form sheets which may be used to form various prosthetic devices such as vascular grafts, muscle grafts, bone fillers, etc. Alternatively the filaments can be formed into non-woven fabrics by lamination with or without additional polymeric matrix. Such non-woven fabrics may be used for the same purposes as the woven fabrics listed above.

The composite biocompatible sheets disclosed herein may also be used to form prosthetic devices. Devices may be formed by molding the composite sheets into the above named devices. The sheets may also be formed into other surgical implants such as surgical clips, surgical fasteners, staples, bone pins, bone screws, anastomosis rings, wound dressings, drug delivery devices, etc.

Figure 6:
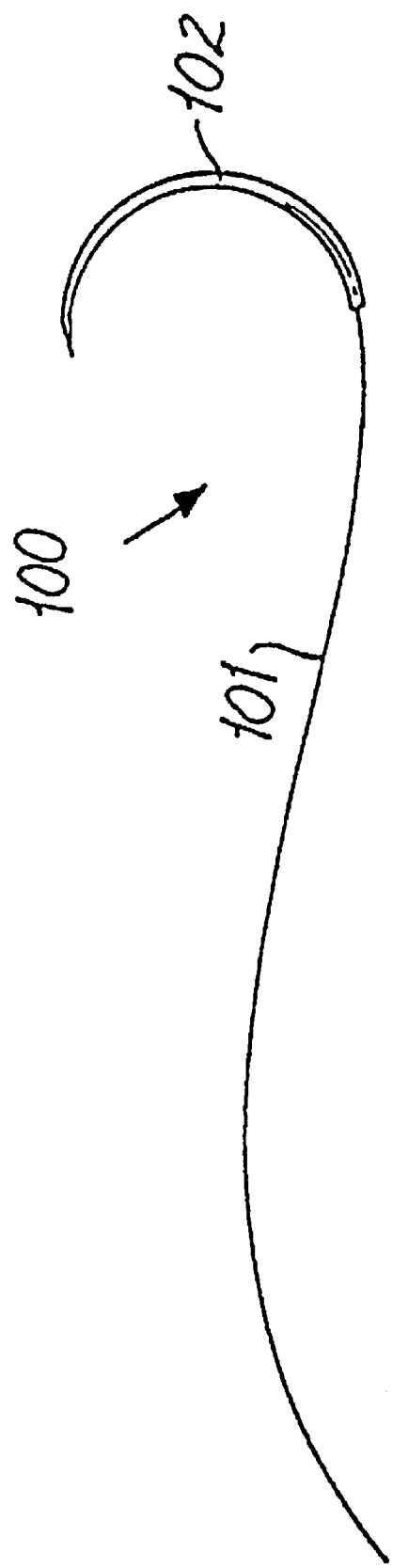
FIG. 6 illustrates a surgical needle suture combination according to the present invention.

A suture in accordance with the present disclosure, suture, may be attached to a surgical needle 100 as shown in FIG. 6 by methods well known in the art. Wounds may be sutured by approximating tissue and passing the needle suture through tissue to create wound closure. The needle preferably is then removed from the suture and the suture tied.

It is within the scope of this disclosure to coat or impregnate the biocompatible composite materials disclosed herein as well as implants and prosthetic devices made therefrom with one or more materials which enhance its functionality, e.g., surgically useful substances, such as those which accelerate or beneficially modify the healing process when the material is implanted within a living organism. Thus, for example, antimicrobial agents such as broad spectrum antibiotics (gentamicin sulphate, erythromycin or derivatized glycopeptides) which are slowly released into the tissue can be incorporated to aid in combating clinical and sub-clinical infections in a surgical or trauma wound site.

To promote wound repair and/or tissue growth one or several substances can be introduced into the present composite biocompatible materials or impregnated into fabrics or prostheses made from the composite biocompatible materials. Exemplary substances include polypeptides such as human growth factors. The term "human growth factor" or "HGF" embraces those materials, known in the literature, which are referred to as such and includes their biologically active, closely related derivatives. The HGFs can be derived from naturally occurring sources and are preferably produced by recombinant DNA techniques. Specifically, any of the HGFs which are mitogenically active and as such effective in stimulating, accelerating, potentiating or otherwise enhancing the wound healing process are useful herein. Growth factors contemplated for use include HEGF (urogastrone), TGF-beta, IGF, PDGF, FGF, etc. These growth factors, methods by which they can be obtained and methods and compositions featuring their use to enhance wound healing are variously disclosed, iAbram in U.S. Pat. Nos. 3,883,497; 3,917,824; 3,948,875; 4,338,397; 4,418,691; 4,528,186, 4,621,052; 4,743,679 and 4,717,717; European Patent Applications 0 046 039; 0 128 733; 0 131 868; 0 136 490; 0 147 178; 0 150 572; 0 177 915 and 0 267 015; PCT International Applications WO 83/04030; WO 85/00369; WO 85/01284 and WO 86/02271 and UK Patent Applications GB 2 092 155 A; 2,162,851 A and GB 2 172 890 A, all of which are incorporated by reference herein. When incorporating wound healing substances such as those discussed above, it may be advantageous to use composite materials having at least one shell layer are formed from a bioabsorbable material having a relatively high rate of bioabsorption. By incorporating wound healing substances in a high rate bioabsorption layer, the substance will be more quickly absorbed while the remaining composite material will still retain sufficiently good mechanical properties to perform its medical or surgical function.

To decrease abrasion, increase lubricity, etc., the biocompatible composite materials can be coated with various substances. Copolymers of glycolide and lactide and polyethylene oxide, calcium salts such as calcium stearate, compounds of the pluronic class, copolymers of caprolactone, caprolactone with PEO, polyHEMA, etc. may be employed.

EXAMPLE 1

Table I below sets forth typical conditions for extruding, stretching composite bioabsorbable monofilament sutures in accordance with this disclosure.

TABLE I

CONDITIONS OF MANUFACTURING COMPOSITE MONOFILAMENT

| Suture Size | 3/0 | |
|---|---|---|
| Material | Polycaprolactone | Polydioxanone |
| Process Conditions | Extrusion Operation | |
| Extruder | Extruder 1 (shell) | Extruder 2 (core) |
| extruder screw, rpm | 0.6 | 1.3 |
| pump rpm | 4.4 | 5.8 |
| barrel temp., °C., zone A | 80 | 52 |
| barrel temp., °C., zone B | 120 | 135 |
| barrel temp., °C., zone C | 120 | 135 |
| clamp temp., °C. | 120 | 135 |
| adapter temp., °C. | 120 | 130 |
| pump temp., °C. | 120 | 135 |
| barrel melt temp, °C. | 117 | 149 |
| pump melt temp., °C. | 117 | 150 |
| spinneret melt temp., °C. | 118 | 118 |
| barrel pressure, psi | 760 | 1250 |
| pump pressure, psi | 500 | 1000 |
| spinneret pressure, psi | 840 | 1980 |
| pump size, cc per revolution | 0.16 | 0.16 |
| outside diameter of spinneret orifices, mm | 0.28 | — |
| inside diameter of spinneret orifices, mm | — | 0.25 |
| quench bath temp., °C. | 18 | 18 |
| Stretching (Orienting) Operation | | |
| draw bath temp., °C. | 50 | |
| first godet, mpm | 4.2 | |
| second godet, mpm | 19.7 | |
| second oven temp., °C. | 70 | |
| third godet, mpm | 24.6 | |
| draw ratio | 5.9:1 | |
| Annealing Operation EXAMPLE | | |
| oven temp., °C. | 50 | |
| time (hrs.) | 18 | |

The physical properties of the sutures and the procedures employed for their measurement are set forth in Table II as follows:

TABLE II

PROCEDURES FOR MEASURING PHYSICAL PROPERTIES OF COMPOSFIE MONOFILAMENT SUTURES

| Physical Property | Test Procedure |
|---|---|
| knot-pull strength, kg | U.S.P. XXI, tensile strength, sutures (881) |
| straight-pull strength, kg | ASTM D-2256, Instron Corporation |
| elongation, % | ATSM D-2256 |
| tensile strength, kg/mm$^2$ | ASTM D-2256, Instron Corporation Series IX Automated Materials Testing System 1.03A |

Table III below sets forth the physical properties of the composite monofilament suture of Example 1.

TABLE III

| Physical Property | |
|---|---|
| diameter (mm) | 0.295 |
| shell thickness (mm) | 0.036 |
| core thickness (mm) | 0.223 |
| knot-pull strength (kg) | 2.2 |
| straight-pull strength (kg) | 3.0 |
| elongation (%) | 26 |
| tensile strength (kg/mm$^2$) | 47 |

EXAMPLE 2

In another embodiment, a polypropylene monofilament suture is prepared having a syndiotactic polypropylene shell and an isotactic polypropyelene core. The monofilament contains 12% by weight syndiotactic polypropylene. Conditions which may be employed to manufacture such a monofilament by co-extrusion are provided in Table IV.

TABLE IV

CONDITIONS OF MANUFACTURING COMPOSITE POLYPROPYLENE MONOFILAMENT

| Suture Size | 3/0 | |
|---|---|---|
| Material | Syndiotactic Polypropylene | Isotactic Polypropylene |
| Process Conditions | Extrusion Operation | |
| Extruder | Extruder 1 (shell) | Extruder 2 (core) |
| extruder screw, rpm | 0.3 | 4.4 |
| pump rpm | 1.8 | 13.4 |
| barrel temp., °C., zone A | 153 | 185 |
| barrel temp., °C., zone B | 159 | 188 |
| barrel temp., °C., zone C | 162 | 190 |
| clamp temp., °C. | 163 | 190 |
| adapter temp., °C. | 162 | 196 |
| pump temp., °C. | 162 | 190 |
| barrel melt temp, °C. | 159 | 175 |
| pump melt temp., °C. | 175 | |
| spinneret melt temp., °C. | 171 | 192 |
| barrel pressure, psi | 640 | 970 |
| pump pressure, psi | 500 | 500 |
| spinneret pressure, psi | 360 | — |
| pump size, cc per revolution | 0.16 | 0.16 |
| outside diameter of spinneret orifices, mm | 0.28 | — |
| inside diameter of spinneret orifices, mm | — | 0.25 |
| quench bath temp., °C. | 18 | 18 |
| | Stretching (Orienting) Operation | |
| first godet, mpm | 5.6 | |
| first oven temp., °C. | 150 | |
| second godet, mpm | 53.2 | |
| second oven temp., °C. | 150 | |
| third godet, mpm | 43.3 | |
| draw ratio | 7.7:1 | |
| | Annealing Operation | |
| oven temp., °C. | 80 | |
| time (hrs.) | 1 | |

TABLE V

Table V below sets forth the physical properties of the composite monofilament suture of Example 2 tested using the techniques described in Table II, above. For purposes of comparison, the physical characteristics of two commercially available size 3/0 polypropylene sutures are also provided in Table V.

TABLE V

| | | Commercially Available 3/0 Polypropylene Sutures | |
|---|---|---|---|
| Physical Property | Example 2 | A | B |
| diameter (mm) | 0.237 | 0.25 | 0.244 |
| shell thickness (mm) | 0.064 | — | — |
| core thickness (mm) | 0.173 | — | — |
| knot-pull strength (kpsi) | 54 | 48 | 49 |
| straight-pull strength (kpsi) | 79 | 70 | 61 |
| elongation (%) | 35 | 34 | 39 |
| modulus (kpsi) | 410 | 384 | 345 |
| Friction coefficient | 0.33 | 0.4 | 0.38 |

It will be understood that various modifications may be made to the embodiments disclosed herein. For example, composite medical or surgical articles having a composite core/shell structure may be formed directly by coextrusion, injection molding, casting, etc. Composite materials having a core/shell structure may also be fabricated by lamination bonding techniques, e.g., hot isostatic pressing. Such techniques also result in composite materials whose mechanical properties may be described using the above rule of mixtures equation. Therefore, the above description should not be construed as limiting, but merely as exemplifications of preferred embodiments. Those skilled in the art will envision other modifications within the scope and spirit of the claims appended hereto.

What is claimed is:

1. A surgical needle-suture combination comprising:
    a surgical needle;
    a suture attached to said needle;
    the suture comprising a monofilament having a core portion formed from isotactic polypropylene, a shell portion formed from syndiotartic polypropylene, and a micro-shell layer including a mixture of isotactic and syndiotactic polypropylene joining the core to the shell at the interface between the core and shell portions.

2. A surgical needle-suture combination as in claim 1 wherein the core comprises between about 70 and about 95 percent by volume of the monofilament.

3. A surgical needle-suture combination as in claim 1 wherein the core comprises between about 80 and about 90 percent by volume of the monofilament.

4. A biocompatible composite implantable within a living organism comprising:
    a core portion formed from a first biocompatible, non-bioabsorbable polymeric material, a shell portion formed from a second biocompatible, non-bioabsorbable polymer material, wherein the first and second biocompatible polymeric materials are chemically distinct and are each selected from the group consisting of polyesters, polyamides, polyurethanes, polycarbonates, polyimides, fluoropolymers, polyolefins and vinyl polymers, and a micro-shell layer including a mixture of the first and second biocompatible, non-bioabsorbable polymer materials joining the core to the shell at the interface between the core and shell portions.

5. A composite as in claim 4 wherein the core portion is made of a polyester.

6. A composite as in claim 5 wherein the shell portion is made of a polyurethane.

7. A composite as in claim 4 wherein the core portion is made of a polyamide.

8. A composite as in claim 7 wherein the core portion is made of a low order nylon and the shell portion is made of a high order nylon.

9. A composite as in claim 4 wherein the core portion is made of a polyolefin.

10. A composite as in claim 9 wherein the core portion is made of isotactic polypropylene.

11. A composite as in claim 10 wherein the shell portion is made of syndiotactic polypropylene.

12. A composite as in claim 4 in the form of a monofilament.

13. A suture formed from the filament of claim 12.

* * * * *